(12) United States Patent
Holwerda et al.

(10) Patent No.: US 6,846,847 B2
(45) Date of Patent: Jan. 25, 2005

(54) BIOCIDAL AGENTS AND METHODS OF USE

(76) Inventors: James G. Holwerda, 1217 W. Paseo Del Mar, San Pedro, CA (US) 90731-6060; Bruce D. Levine, 2347 Colt Rd., Rancho Palos Verdes, CA (US) 90295-6575

( * ) Notice: Subject to any disclaimer, the term of this patent is extended or adjusted under 35 U.S.C. 154(b) by 0 days.

(21) Appl. No.: 10/202,787

(22) Filed: Jul. 24, 2002

(65) Prior Publication Data

US 2004/0024020 A1 Feb. 5, 2004

(51) Int. Cl.$^7$ .................. A61K 31/05; A61K 31/19; A61K 31/22
(52) U.S. Cl. .................. 514/731; 514/546; 514/552; 514/557; 514/558
(58) Field of Search .................. 514/546, 552, 514/557, 558, 731

(56) References Cited

U.S. PATENT DOCUMENTS

| | | | | |
|---|---|---|---|---|
| 3,729,519 A | * | 4/1973 | Brossi et al. | 568/644 |
| 4,668,419 A | * | 5/1987 | Moseman | 424/770 |
| 4,957,730 A | | 9/1990 | Bohn et al. | |
| 5,658,584 A | * | 8/1997 | Yamaguchi | 424/405 |
| 6,013,677 A | * | 1/2000 | Dyer | 514/643 |

FOREIGN PATENT DOCUMENTS

| | | | |
|---|---|---|---|
| DE | 2 312 280 | * | 9/1974 |
| EP | 0 273 202 B1 | * | 6/1995 |

OTHER PUBLICATIONS

Principles and Practice of Infectious Diseases (4th Ed. 1995), p. 2377.*

Shapiro et al., "Inhibition of Oral Bacteria by Phenolic Compound. Part 1. QSAR Anaysis using Molecular Connectivity",Quant. Struct.–Act. Relat., vol. 17, pp. 327–337.*

STN/CAS online, file CAPLUS, Acc. No. 1976:472848, Doc. No. 85:72848 (Furukawa et al., Yukagaku (1976), vol. 25, No. 6, pp. 358–361), Abstract.*

Attygalle, et al.; "Chemical Composition and Function of Metapleural Gland Secretion of the Ant, *Crematogaster deformis* Smith (Hymenoptera: Myrmicinae)"; *Journal of Chemical Ecology* 15:1 (1989), pp. 317–328.

Do Nascimento et al.; "Chemistry of Metapleural Gland Secretions of Three Attine Ants, *Atta sexdens rubropilosa, Atta cephalotes*, and *Acromyrmex octospinosus* (Hymenoptera: Formicidae)"; *Journal of Chemical Ecology* 22:5 (1996), pp. 987–1000.

Ortius–Lechner et al.; "Metapleural Gland Secretion of the Leaf–Cutter Ant *Acromyrmex octospinosus*: New Compounds and Their Functional Significance"; *Journal of Chemical Ecology* 26:7 (2000), pp. 1667–1683.

* cited by examiner

*Primary Examiner*—S. Mark Clardy
*Assistant Examiner*—Frank Choi
(74) *Attorney, Agent, or Firm*—Townsend and Townsend and Crew LLP

(57) ABSTRACT

The present invention provides antimicrobial compositions and methods for treating medical conditions in mammals. The compositions provided herein are based on the surprising discovery that the metapleural gland extract from ants has biocidal activity that is useful against a variety of microorganisms, including bacteria, fungi and viruses. Accordingly, it has been discovered that the components of the metapleural gland extract are useful for the treatment and prevention of disease in mammals. The present invention provides a number of antimicrobial compounds which kill bacteria, fungi and viruses upon contact. In addition, the present invention provides methods for treating microorganism growths in mammals, including application of the antimicrobial compositions provided herein.

11 Claims, 5 Drawing Sheets

BIOCIDAL AGENTS AND METHODS OF USE

BACKGROUND OF THE INVENTION

Ants reside in, among other places, nests located in underground cavities they have excavated in the soil, in rotting wood, or in other locations which provide an ideal environment for microorganisms such as bacteria and fungi to thrive. Although both bacteria and fungi are potential serious health hazards for ants, ant colonies are rarely afflicted by bacterial or fungal infections. This remarkable immunity to such infections can be attributed to the secretions from the metapleural gland, which is located in the thorax of adult ants.

The substances secreted by the metapleural gland of ants provide a mixture of chemicals which is highly effective in killing or preventing the growth of microorganisms such as bacteria and fungi. The metapleural gland is a paired structure at the posterolateral end of the alitrunk, and is found only in ants (see, Holldobler and Engel-Siegel, 1984). The gland has been thought to be involved in the antibiotic defense against microorganisms of many ant species (see, Maschwitz et al., 1970; Maschwitz, 1974). Study of the antibiotic properties of the metapleural gland secretion has identified a number of active chemical compounds and their functions.

It has been suggested that metathoracic (metapleural) gland secretions are involved in the control of foreign bacteria and fungi and possibly viruses in the fungus gardens of *Atta sexdens rubropilosa*, a leaf-cutting ant of Central and South America (see, Attygalle and Morgan, "Chemicals from the Glands of Ants," 1983). The compounds identified in secretions from the metathoracic gland of *Atta sexdens rubropilosa* are primarily carboxylic acids, and include the following: phenylacetic acid (PAA), 3-indoleacetic acid (IAA), 3-hydroxydecanoic acid (myrmicacin), 3-hydroxyoctanoic acid and 3-hydroxyhexanoic acid. PAA and 3-indoleacetic acid have plant growth regulatory activities. Myrmicacin and the two related hydroxy-acids are believed to be used by *Atta sexdens rubropilosa* to prevent germination of undesirable fungal spores. Myrmicacin is known to possess a number of other biocidal properties, including pollen germination-inhibitory activity, animal cell growth-inhibiting activity, and antimicrobial activity (see, T. Iwadara et al., *Yakugaku*, 1979, 28, 309).

In contrast to the carboxylic acid-containing secretion from *A. sexdens*, the metapleural gland chemical secretion from the Australian ant *Crematogaster deformis* consists primarily of phenols (see, Attygalle et al., "Chemical Composition and Function of Metapleural Gland Secretion of the Ant *Crematogaster deformis*, Smith (see, Hymenoptera: Myrmicinae)", *Journal of Chemical Ecology*, Vol. 15, No. 1, 1989). These phenols include: 3-propylphenol, 3-pentylphenol, mellein, 5-propylresorcinol and 5-pentylresorcinol. The secretion from the metapleural gland of *Crematogaster deformis* is also known to have antibacterial and antifungal properties.

Antibacterial and antifungal agents are important for the treatment of many medical conditions. In particular, the treatment of dermatological conditions frequently involves the use of a topical antifungal agent on skin, mucous membranes and hair lesions. Moreover, the danger of hospital-acquired infection has intensified with the rise of new strains of common microbes that are resistant to antibiotics. According to the Centers for Disease Control and Prevention, 5 percent of the people admitted to American hospitals, about 1.8 million patients a year, will pick up an infection there (see, Yoffe, "Unclean Hands, Hospital Dangers," *The New York Times*, Nov. 15, 1999, page 9). Twenty thousand of them will die as a direct result of contracting an infection in the hospital; by contrast, 17,171 Americans died of AIDS in 1998. The infections will cost $4.5 billion to treat, the CDC estimates, and it says better infection control could have prevented one-third of those cases.

Clearly, there currently exists a need for more efficacious antimicrobial agents to treat medical conditions in humans and animals. The present invention, effective against such a surprisingly wide spectrum of organisms, satisfies such a need.

SUMMARY OF THE INVENTION

The present invention provides antimicrobial compositions and methods useful for eradicating microorganisms such as bacteria, fungi and viruses. Advantageously, these compositions and methods are non-invasive and quite efficacious for treating microorganism growth. In addition, the present invention provides methods for treating a microorganism growth in a mammal using such compositions.

In one embodiment, the present invention provides an antimicrobial composition for the treatment of a mammal, the composition comprising a compound of Formula I or II:

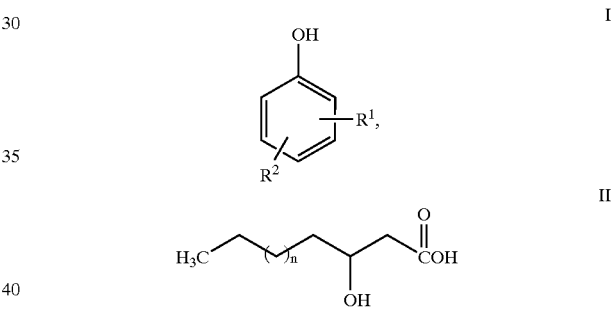

or a combination thereof, and an excipient. $R^1$, in Formula I, is an optionally substituted alkyl group. $R^2$, in Formula I, is hydrogen or a hydroxyl group. In Formula II, the index "n" has a value from about 0 to about 6. In Formulae I and II the compounds may exist as salts. In certain aspects, Formula II may exist as a salt, ester or a combination thereof.

In an alternative embodiment, $R^1$ and $R^2$, in Formula I, and the carbons to which they are attached, join to form an optionally substituted 5- or 6-membered heterocyclic ring.

In a preferred embodiment, the compound of Formula I has the formula:

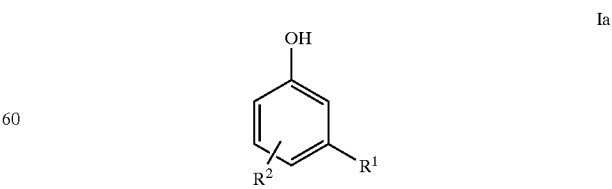

wherein $R^1$ is an optionally substituted alkyl group.

In another preferred aspect, the compound of Formula I has the formula:

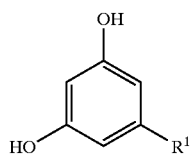

Ib wherein $R^1$ is an optionally substituted alkyl group.

In a preferred aspect of the present invention, $R^1$ of Formula I is $C_1$–$C_8$ alkyl, and more preferably, $R^1$ is a $C_3$–$C_7$ alkyl group such as propyl, butyl or pentyl.

The compound of Formula II is preferably 3-hydroxydecanoic acid. In another aspect, the antimicrobial composition of the present invention comprises a combination of compounds of Formulae I and II.

The antimicrobial composition of the present invention can take a variety of forms. Suitable forms include, but are not limited to, a suspension, a powder, a paste, a jelly, a cream, a shampoo, an ointment, a soap, an emulsion or a spray.

In another aspect, the composition of the present invention has a pH of about 3.0 to 7.0, preferably about 3.0 to 5.5.

In another aspect, the present invention provides a method for inhibiting microorganism growth on a mammal, the method comprising: contacting the mammal with a biocidally effective amount of a composition comprising a compound of Formulae I or II,

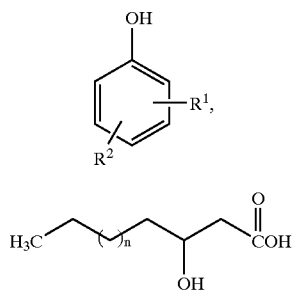

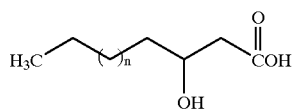

or a combination thereof, and an excipient. $R^1$, in Formula I, is an optionally substituted alkyl group. $R^2$, in Formula I, is hydrogen or a hydroxyl group. In Formula II, the index "n" has a value from about 0 to about 6. In Formulae I and II the compounds may exist as salts. In certain aspects, Formula II may exist as a salt, ester or a combination thereof. In one aspect, the compound of Formula II is 3-hydroxydecanoic acid.

In an alternative embodiment, $R^1$ and $R^2$, in Formula I, and the carbons to which they are attached, join to form an optionally substituted 5- or 6-membered heterocyclic ring.

The biocidal compositions of the present invention are effective against a broad range of microorganisms, including, but not limited to, *Trichophyton rubrum, Candida albicans, Aspergillus fumigatus, Staphylococcus aureus, Beta Streptococcus, Escherichia coli* and combinations thereof.

In another embodiment, the antimicrobial compositions of the present invention are effective against *Tinea pedis, Tinea unguium, Tinea cruris, Tinea capitis* and combinations thereof.

In one aspect, the present invention provides a method for treating onychomycosis, the method comprising contacting an area in need of treatment with a biocidally effective amount of a composition comprising a compound of Formulae I or II,

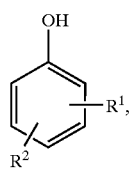

I

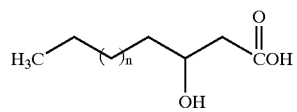

II or a combination thereof, and an excipient. $R^1$, in Formula I, is an optionally substituted alkyl group. $R^2$, in Formula I, is hydrogen or a hydroxyl group. In Formula II, the index "n" has a value from about 0 to about 6. In Formulae I and II the compounds may exist as salts. In certain aspects, Formula II may exist as a salt, ester or a combination thereof.

In an alternative embodiment, $R^1$ and $R^2$, in Formula I, and the carbons to which they are attached, join to form an optionally substituted 5- or 6-membered heterocyclic ring.

The present invention also provides an antimicrobial textile composition. As used herein, the term "textile composition" refers to a textile or fiber which is associated with a compound of Formula I or Formula II, or a combination thereof. The textile compositions of the present invention comprise a compound of Formulae I or II,

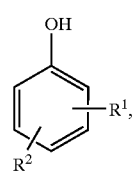

I

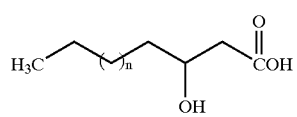

II or a combination thereof, and an excipient. $R^1$, in Formula I, is an optionally substituted alkyl group. $R^2$, in Formula I, is hydrogen or a hydroxyl group. In Formula II, the index "n" has a value from about 0 to about 6. In Formulae I and II the compounds may exist as salts. In certain aspects, Formula II may exist as a salt, ester or a combination thereof.

In a preferred embodiment, the textile composition is in the form of a wipe, a towel, a tampon, a bedding, or a cover. In another embodiment, the textile composition comprises 3-hydroxydecanoic acid.

In still yet another aspect, the present invention provides an antimicrobial composition for the treatment of a mammal, the composition comprising an extract from the metapleural gland of an ant. In one embodiment, suitable ant species include, but are not limited to, *Atta sexdens rubropilosa, Atta cephalotes, Acromyrmex octospinosus, Crematogaster deformis* and combinations thereof. In another embodiment, the extract comprises a compound of Formulae I or II.

These and other aspects will become more apparent when read with the accompanying drawings and detailed description which follow.

DETAILED DESCRIPTION OF THE INVENTION AND PREFERRED EMBODIMENTS

I. General

Figure 1:
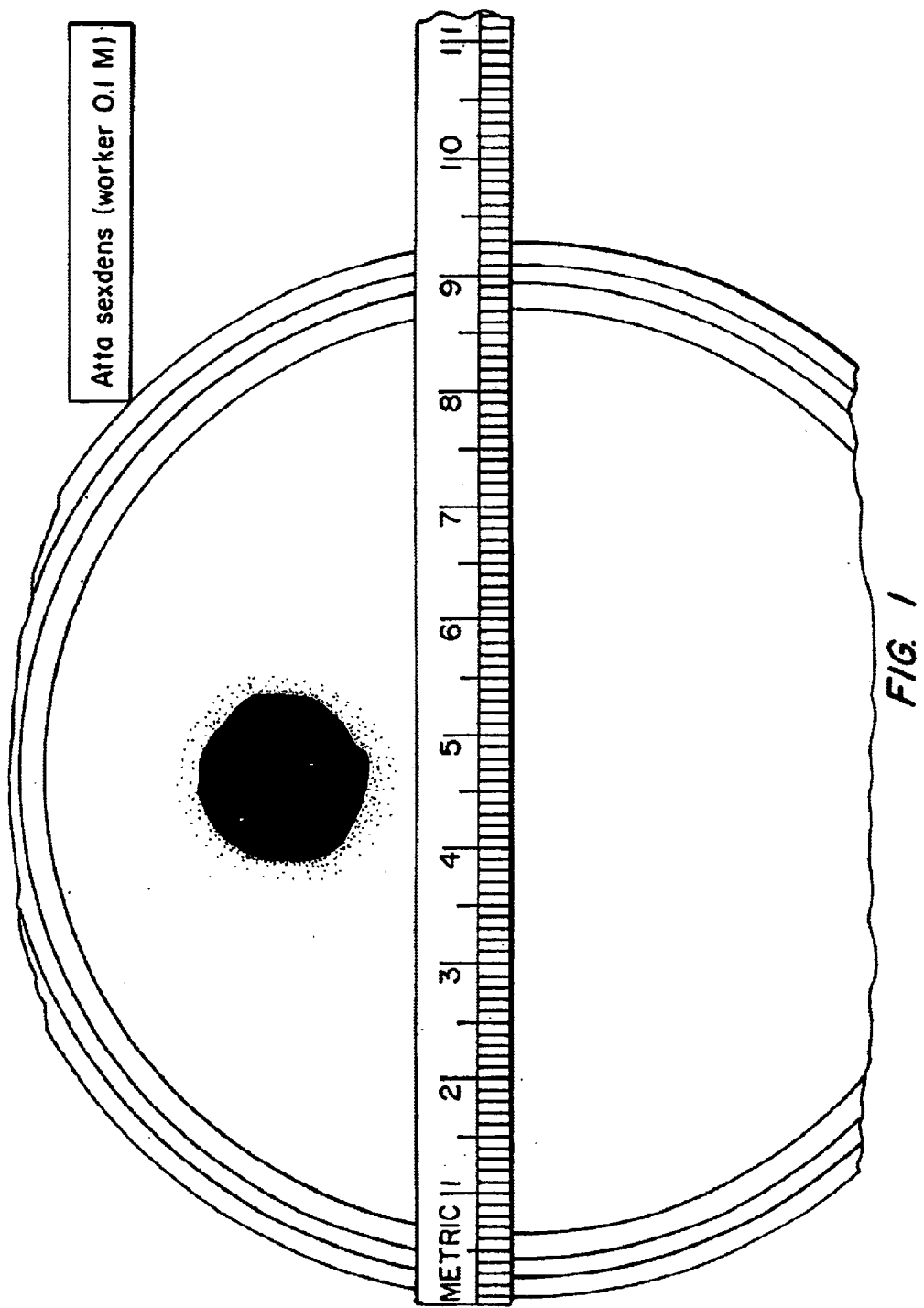
FIG. 1 illustrates the inhibitory effect of a composition of the present invention on *Escherichia coli* growth.

The present invention provides antimicrobial compositions and methods for inhibiting microorganism growth such as on a mammal. Advantageously, these compositions and methods are non-invasive and extremely efficacious for inhibiting microbial growth. The antimicrobial compositions and methods inhibit growth of Gram positive bacteria, Gram negative bacteria, fungi, yeasts, molds and viruses upon contact. Such compositions and methods are effective for inhibiting growth of a variety of microorganisms including, but not limited to, *Trichophyton rubrum, Candida albicans, Aspergillus fumigatus, Staphylococcus aureus, Beta Streptococcus, Escherichia coli* and combinations thereof. These compositions can be administered in stand-alone formulation, in combination therapy or as separate dosage forms administered simultaneously or sequentially.

As used herein, the terms "antimicrobial," "microbiocidal," or "biocidal" refers to the ability to kill at least some types of microorganisms, or to inhibit the growth or reproduction of at least some types of microorganisms such as fungi, bacteria, viruses, parasites and *rickettsiae*. The compositions prepared in accordance with the present invention have microbiocidal activity and uses against a broad spectrum of pathogenic microorganisms. In certain preferred aspects, the compositions of the present invention have microbiocidal activity against microorganism growths such as, for example, *Tinea pedis, Tinea unguium, Tinea cruris,* or *Tinea capitis.*

II. Compositions of the Invention

In the context of the present invention, the term "patient" refers to a subject to which the compounds of the invention can be administered. Preferably, a patient is a mammal, e.g., a rodent; a farm animal or a domesticated animal, such as a horse, a cow, a pig, a sheep, a dog or a cat; a primate or a human. A patient can be affected with a disease, or can be free of detectable disease in which case the compounds and compositions of the present invention are administered prophylactically. In one preferred aspect, the compositions of the present invention can be administered to patients with a microorganism growth, such as, for example, onychomycosis.

In one embodiment, the present invention provides an antimicrobial composition for the treatment of a mammal, the composition comprising a compound of the Formulae I or II:

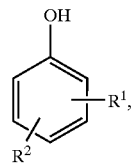

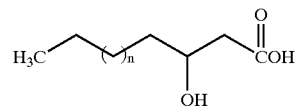

or a combination thereof, wherein $R^1$, $R^2$ and n have previously been defined.

In certain preferred aspects, $R^1$ in Formula I is an optionally substituted alkyl group such as a $C_1$–$C_8$ alkyl, preferably a $C_3$–$C_7$ alkyl group such as propyl, butyl or pentyl. As used herein, the term "alkyl" denotes branched or unbranched hydrocarbon chains, preferably having about 1 to about 8 carbons, such as, methyl, ethyl, n-propyl, isopropyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

Suitable salts of Formulae I or II useful in the present invention include alkaline metal salts such as potassium, sodium and the like. The term "salt" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of acceptable base addition salts include sodium, potassium, calcium, ammonium, organic amino, or magnesium salt, or a similar salt.

Suitable esters of Formula II include alkyl esters of carboxylic acid such as methyl, ethyl and the like. Those of skill in the art will know of other esters suitable for use in the present invention.

In certain aspects the preferred range of Formula II esters present in the compositions of the present invention range from about 1% to 99% by weight; preferably from about 1% to 50% by weight; and more preferably, from about 1% to about 20% by weight.

In one embodiment, the compound of Formula I is phenylacetic acid, wherein $R^1$ is carboxymethyl and $R^2$ is hydrogen. In one preferred embodiment, the composition of the present invention is Formula Ib. In other embodiments, the compositions comprises one or more of the following compounds: 3-n-propylphenol, 3-pentylphenol, 5-propylresorcinol, 4-hexylresorcinol, mellein, phenol, phenylacetic acid, 3-hydroxydecanoic acid, or 3-hydroxyoctanoic acid.

In another embodiment, the compositions of the present invention comprise a compound of Formula I, such as 3-propylphenol, 3-pentylphenol, 3-indoleacetic acid, phenylacetic acid, skatole, mellein and combinations thereof.

In an alternative embodiment, $R^1$ and $R^2$, in Formula I, and the carbons to which they are attached, join to form an optionally substituted 5- or 6-membered heterocyclic ring. The term "heterocyclic ring," means a cyclic hydrocarbon radical having the specified number of atoms consisting of carbon atoms and from one to three heteroatoms selected from the group consisting of O, N, and S, and wherein the nitrogen and sulfur atoms can optionally be oxidized and the nitrogen heteroatom can optionally be quaternized. In certain aspects, $R^1$ and $R^2$ join to form skatole or indoleacetic acid as set forth below.

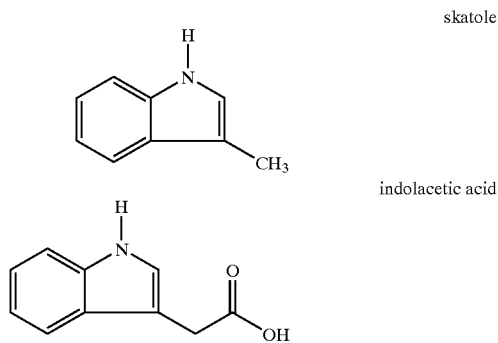

skatole indolacetic acid

In another aspect, $R^1$ and R2 join to form a 6-membered substituted lactone such as mellein.

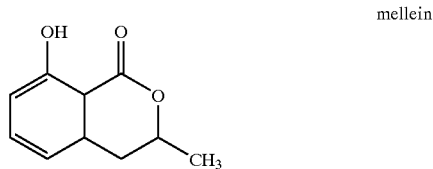

mellein

In general, the compounds of the present compositions are avaiable from commercial sources. In some instances, the compounds of the present invention can be extracted and purified from ant metapleural gland secretions. The procedure for preparing ant metapleural gland extracts is described in Example 7 set forth below. In other instances, the compounds of the present invention can be synthesized using the methods known to those of skill in the art.

The antimicrobial compounds of the present invention are useful as solo active ingredients, in combination with other compounds of the invention or with other antimicrobial agents. When the antimicrobial compounds of the present invention are used in combination with other compounds of the invention, the result is, surprisingly, a synergistic effect. The combination of antimicrobial compounds enhances the antimicrobial activity of the individual active ingredients in the composition. The phrase "synergistic effective amount" refers to a combined amount of both a compound of Formula I and a compound of Formula II or two compounds of Formula I or two compounds of Formula II that is effective to cause a synergistic effect. Synergy is a biological phenomenon in which the effectiveness of two active components in a mixture is more than additive, i.e., the effectiveness is greater than the equivalent concentration of either component alone. In certain aspects, the effectiveness of the combination compounds of the present invention is synergistic. Thus, synergism is a result, or function, that is more than the sum of the results, or functions of individual elements.

In certain embodiments, the present invention provides an antimicrobial composition comprising a combination of at least two active components combined in an amount ranging from about 1:1 to 10:1 by weight. In a preferred embodiment, the active components are combined at a ratio of about 1:1 to 1:5 by weight. In another preferred embodiment, the active components are combined at a ratio of about 1:1 to 1:3 by weight, more preferably in an amount of about 1:1 by weight. Preferred combinations include ratios of: 1:1, 1.5:1, 1:1.5, 1:2, and 2:1 by weight.

For example, in one embodiment the combination ratio of Formula I and Formula II is about 1:5 to about 5:1. In another embodiment, the ratio is 1:2 to about 2:1. In still other aspects, the ratio is about 1:1.

In another embodiment, the compositions of the present invention provides an ant metapleural gland extract. All ants at present are classified as a single family, the *Formicidae*, which include 11 subfamilies, 297 genera and, at the present time, approximately 8,800 species (see, B. Holldobler and Edward O. Wilson, 1990, *The Ants*, p. 4,). Almost all ants have a metapleural gland. In certain aspects, the metapleural gland extract is from ant species including, but not limited to, *Atta sexdens rubropilosa, Atta cephalotes, Acromyrmex octospinosus, Crematogaster deformis* and combinations thereof.

In this aspect, the extract preferably comprises at least one of the following compounds: 3-propylphenol, 3-pentylphenol, 3-hydroxydecanoic acid, 3-indoleacetic acid, phenylacetic acid, skatole, and mellein.

In one aspect, the ant metapleural gland secretions are collected in fine glass capillaries (50 to 70-μm diameter at one end). The larger end of the capillary is attached to a 10-μl syringe needle with a silicone tubing connection. The wall of the bulla of the metapleural gland is pierced with a fine insect-mounting pin, and the ant is then held so the fine tip of the capillary is inserted into the hole in the bulla, and the secretion is withdrawn into the capillary by gently raising the plunger of the syringe. The collected secretion can then be used directly, or extracted with solvent prior to use in the compositions of the present invention.

Antimicrobial compositions according to the present invention can also be utilized in combination with other antimicrobial ingredients. By adding antimicrobial compositions according to the invention the antimicrobial activity of other ingredients can be further enhanced.

Additional ingredients which can be used in combination are not specifically limited as long as they are known antimicrobial substances. Considering safety for human beings, naturally-occurring substances may be preferably utilized. Examples of suitable substances are essential oils such as lacquer, thyme oil, clove oil, black pepper oil, peppermint oil, mace oil, nutmeg oil, orange oil, sandalwood oil, cedarwood oil, cypress oil, and cinnamon oil, and essential oil ingredients such as phenol derivatives such as thymol, euganic, carvacrol, dihydroguaiaretic acid, alcohols such as geraniol, citronellol, nerolidole, and farnesol, aldehydes such as citral, citronellal, and cinnamic aldehyde, lactones such as γ-decalactone δ-decalactone, monoglycerides such as monocaprin and monolaurin, and organic acids such as cinnamic acid, decanoic acid and senecionic acid.

When antimicrobial compositions of the present invention are combined with other antimicrobial ingredients, the amount of the compositions in relation to that of the additional ingredients is preferably about 1:1 to 10:1, more preferably about 1:1 to 5:1, and most preferably about 1.5:1.

In one embodiment, the benefits of the compounds of Formula I or II are enhanced at low pH. For example, in one aspect, the acid of Formula II when present in its protonated form is more efficacious. The pH of the compositions of the present invention can be adjusted to a sufficiently low level so that the acid of Formula II exists primarily in an undissociated acid state. The pH of the compositions of the present invention can be adjusted and preferably buffered to have a range of from about 3.0 to about 7.0, preferably from about 3 to about 6.0 and more preferably from about 4.4 to about 5.5.

III. Dosage Forms

One of skill in the art will appreciate that suitable formulations are dependent on the form of delivery to be employed, and all such forms are contemplated by the present invention. additionally, in some embodiments, combinations of agents are employed in a single formulation, while in other embodiments, agents are fonnulated separately, but administered in combination, or sequentially. Compositions of single agents will be understood to also include compositions of two or more agents. Still further, different formulations can be used for those embodiments in which agents are administered separately or sequentially, by different routes of administration.

The compounds of the present invention can be formulated to be administered using any of a variety of routes, preferably, topical administration, such as, e.g., to the skin for prophylactic and/or therapeutic treatment.

The present compounds can be incorporated into a variety of compositions for therapeutic and/or prophylactic administration. A number of suitable formulations for use in the present invention are found in Remington, *Pharmaceutical Sciences*, Mack Publishing Company, Philadelphia, Pa., 17th ed. (1985); and in *Dermatological Formulations: Percutaneous absorption*, Barry (Ed.), Marcel Dekker Inc. (1983). Moreover, for a brief review of methods for drug delivery, see, Langer (1990) *Science* 249:1527–1533. The antimicrobial compositions described herein can be manufactured in a manner that is known to those of skill in the art, i.e., by means of conventional mixing, dissolving, levigating, emulsifying, encapsulating, entrapping or lyophilizing processes. It will be appreciated that the present methods and excipients are merely exemplary and are in no way limiting.

In order to achieve the mildness required of the present invention, optional ingredients to enhance the mildness to the skin can be added. These ingredients include cationic and nonionic polymers, co-surfactants, moisturizers and mixtures thereof. Polymers useful herein include polyethylene glycols, polypropylene glycols, hydrolyzed silk proteins, hydrolyzed milk proteins, hydrolyzed keratin proteins, guar hydroxypropyltrimonium chloride, polyquats, silicone polymers and mixtures thereof. When used, the mildness enhancing polymers comprise from about 0.1% to about 1%, preferably from about 0.2% to about 1.0%, and more preferably from about 0.2% to about 0.6%, by weight of the rinse-off antimicrobial cleansing composition, of the composition. Co-surfactants useful herein include nonionic surfactants such as the Genapol® 24 series of ethoxylated alcohols, POE(20) sorbitan monooleate (Tween® 80), polyethylene glycol cocoate and Pluronic® propylene oxide/ethylene oxide block polymers, and amphoteric surfactants such as alkyl betaines, alkyl sultaines, alkyl amphoacetates, alkyl amphodiacetates, alkyl amphopropionates, and alkyl amphodipropionates. When used, the mildness enhancing cosurfactants comprise from about 20% to about 70%, preferably from about 20% to about 50%, by weight of the anionic surfactant, of the composition.

In one embodiment, the present invention relates to antimicrobial compositions in a form such as a suspension, a paste, a jelly, a cream, a shampoo, an ointment, a soap, an emulsion or a spray composition. The composition can be mixed under sterile conditions with a pharmaceutically acceptable carrier, and with any preservatives, buffers, or propellants, which may be required. Topical preparations can be prepared by combining the compound of interest with conventional pharmaceutical diluents and carriers commonly used in topical dry, liquid, cream and aerosol formulations. Jellies, ointments and creams can, for example, be formulated with an aqueous or oily base with the addition of suitable thickening and/or gelling agents. Such bases may include water and/or an oil, such as liquid paraffin, or a vegetable oil, such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like. Shampoos can be formulated with an aqueous or oily base and, in general, also include one or more of the following: stabilizing agents, emulsifying agents, dispersing agents, suspending agents, thickening agents, coloring agents, perfumes, and the like. Powders can be formed with the aid of any suitable powder base, e.g., talc, lactose, starch, and the like. Sprays can be formulated with an aqueous base or non-aqueous base also comprising one or more dispersing agents, suspending agents, solubilizing agents, and the like.

The ointments, pastes, creams and jellies also can contain excipients, such as animal and vegetable fats, lacquers, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The dosage of a specific compound depends upon many factors that are well known to those skilled in the art, for example, the particular compound; the condition being treated; the age, weight, and clinical condition of the recipient patient; and the experience and judgment of the clinician or practitioner administering the therapy. An effective amount of the compound is that which provides either subjective relief of symptoms or an objectively identifiable improvement as noted by the clinician or other qualified observer. The dosing range varies with the compound used, the route of administration and the potency of the particular compound.

IV. Methods of the Invention

In one embodiment, the present invention provides a method for inhibiting microorganism growth on a mammal, comprising: contacting the mammal with a biocidal effective amount of a composition comprising compound of Formula I, Formula II, or a combination thereof, wherein $R^1$, $R^2$ and n have been previously defined, thereby inhibiting microorganism growth.

The phrase "biocidally effective amount" refers to the amount of an active agent sufficient to induce a desired biological result. That result may be alleviation of the signs, symptoms, or causes of an infection or any other desired alteration of a biological system.

In one preferred embodiment, the present invention provides methods for the treatment of onychomycosis. Onychomycosis refers to the invasion of the nail plate by a fungus, such as dermatophytes, yeasts, saprophytes, bacteria and other fungi (non-dermatophytic). The term "*Tinea unguium*" is used to describe invasive dermatophytic onychomycosis. When the infection is due to a dermatophyte, both "ringwonn of the nail," "*Tinea pedis*" and "*Tinea unguium*" are sometimes used as synonyms. Dermatophytes that commonly cause onychomycosis include: *Epidermophyton floccosum, Microsporum audouinii, Microsporum canis, Microsporum gypseum, Trichophyton mentagrophytes, Trichophyton rubrum, Trichophyton schoenleinii, Trichophyton tonurans*. Other microorganisms that can cause onychomycosis include: *Acremonium* sp., *Aspergillus* spp., *Candida* spp., *Fusarium oxysporum, Scopulariopsis brevicaulis, Onychocola canadensis, Scytalidium dimidiatum*. The compositions and methods of the present invention are efficacious and effective treatment against all such causes.

The terms "treatment," "therapy," and the like, include, but are not limited to, changes in the recipient's status. The changes can be either subjective or objective and can relate to features such as symptoms or signs of the infection or condition being treated. For example, if the patient notes decreased itching, reduced redness, or decreased pain, then successful treatment has occurred. Similarly, if the clinician notes objective changes, such as a decrease in inflammatory lesions or other abnormalities upon examination of the patient, the treatment has been successful. Prevention of deterioration of the recipient's status is also included by the term. Therapeutic benefit includes any of a number of subjective or objective factors indicating a response of the condition being treated.

The present invention further provides methods of using the compositions above in combination with other known antimicrobial agents, for example miconazole, clotrimazole and the like. Each of the compositions will typically be in a pharmaceutically acceptable dosage form as an effective treatment for a medical condition such as, for example, candidiasis, ringworm, and Tinea versicolor. These pharmaceutical preparations are also useful in treating conditions resulting from the growth of a microorganism, such as, for example, a fungus, a bacteria or a virus, on a mammal. Such preparations are generally administered topically.

Preferred compounds of the compositions include, but are not limited to, 3-hydroxydecanoic acid, 3-n-propylphenol, 3-pentylphenol, 5-propylresorcinol, 4-hexylresorcinol, phenol, phenylacetic acid, 3-hydroxoctanoic acid, 3-hydroxydecanoic acid and 3-hydroxydodecanoic acid. The compositions above may also comprise metapleural gland extract from an ant such as, for example, *Atta sexdens, Atta cephalotes*, or *C. deformis*.

Additional methods provided by the present invention are those in which two or more agents selected from 3-hydroxydecanoic acid, 3-n-propylphenol, 3-pentylphenol, 5-propylresorcinol, 4-hexylresorcinol, mellein, phenol, phenylacetic acid, 3-hydroxoctanoic acid, indoleacetic acid, 3-hydroxydecanoic acid, 3-hydroxydodecanoic acid, and metapleural gland extract from an ant such as, for example, *Atta sexdens, Atta cephalotes*, or *C. deformis*, are administered either in combination or sequentially to provide an enhanced therapeutic benefit. In particular, in certain aspects, the 3-pentylphenol and a second agent from those provided above can provide a greater therapeutic benefit than equally effective doses of 3-pentylphenol alone.

V. Antimicrobial Cleansing Compositions

The term "antimicrobial cleansing composition" as used herein means a composition suitable for application to a surface for the purpose of removing dirt, oil and the like which additionally reduces the number of germs on the surface. Advantageously, the compositions herein are effective against Gram positive bacteria, Gram negative bacteria, fungi, yeasts, molds, and viruses. Preferred embodiments of the present invention are cleansing compositions suitable for use on human skin.

Antimicrobial cleansing products have been marketed in a variety of forms for some time. Forms include deodorant soaps, hard surface cleaners, and surgical disinfectants. These traditional rinse-off antimicrobial products have been formulated to provide bacteria reduction during washing. For example, liquid antibacterial soaps, when used in hand washing, have been found to reduce the amount of the bacteria on the skin by from about 2.0 log (97%) to about 2.5 log (99.7%) in one 30 second handwash, as measured by standard Health Care Personal Handwash tests. That is, skin washed with these soaps were contaminated with only 0.3%–3% of the number of bacteria compared to before washing. Antimicrobial liquid cleansers are disclosed in U.S. Pat. No. 4,847,072, Bissett et al., issued Jul. 11, 1989, in U.S. Pat. No. 4,939,284, Degenhardt, issued Jul. 3, 1990, and U.S. Pat. No. 4,820,698, Degenhardt, issued Apr. 11, 1989, all of which are incorporated herein by reference.

The antimicrobial cleansing composition of the present invention comprises from about 0.001% to about 5%, preferably from about 0.01% to about 2%, more preferably from about 0.05% to about 1.5% and more preferably from about 0.1% to about 1.0%, by weight of an antimicrobial active of the antimicrobial cleansing composition. The exact amount of antibacterial active to be used in the compositions will depend on the particular active utilized since actives vary in potency.

Antimicrobial cleansing compositions of the present invention include, for example, an antimicrobial sanitizing lotion, an antimicrobial contact lens care composition, an antimicrobial skin cleanser, an antimicrobial rinse-off liquid soap, and the like.

VI. Antimicrobial Wipes and Towels

In another embodiment, the present invention relates to antimicrobial wipes and towels. Such wipes and towels can be readily prepared. For example, in one aspect, a process to saturate the paper, wipe such as a cloth wipe, or towel with the antimicrobial compositions described herein can be used. Once prepared, the wipes and towels of the present invention have a broad spectrum of biocidal activity against pathogenic microorganisms.

In one embodiment, the present invention provides antimicrobial compositions in the form of a wipe, a towel, a tampon, a bedding, or a cover. The wipes and towels suitable for the present invention include, but are not limited to, naturally occurring fibers from plants, such as cellulose, cotton, linen, hemp, jute and ramie. They include polymers from animals, based upon proteins and include, but are not limited to, wool, mohair, vicuna and silk. Wipes, towels and the like also include manufactured fibers based upon natural organic polymers which include, but are not limited to, acrylic, aramid, nylon, olefin, polyester, spandex, vinyon, vinyl and graphite.

Further, the wipes or towels or compositions can be useful for food contact surfaces. The microbiology of the food contact surface is important in determining the propensity to biohazards from pathogenic microorganisms. Growth of bacteria on surfaces can be expressed in the following processes (see, VanLoosdrect, M. C. M. et al., *Microbiol. Rev.* 54 (1): 75 1990 and Vigo, T. L., Protective clothing effective against biohazards, *Biotechnology and Bioactive Polymers*, Gebelein, C. and Carraher, C. Eds. 225, Plenum Press. 1994): (1) transport of microorganisms by contact-transmission, diffusion, and others; (2) initial adhesion of the bacteria on the surface; (3) attachment of polymers and fibrils; and (4) formation of microcolonies and biofilm on the surface. The compositions of the present invention are effective against all such processes.

Many pathogenic and spoilage bacteria form biofilms on materials commonly used in food processing and home food cooking, such as wood and plastic cutting boards and containers. The surfaces contaminated by the pathogenic bacteria are sources of cross-contamination of diseases. The compositions of the present invention are effective in eliminating surface cross-contamination and providing safe food-contamination and providing safe food-contact surfaces and containers.

Various foodborne bacteria and microorganisms flourish on food contact and preparation materials and articles. If raw meat, poultry, egg dishes and other foods are not separated, these bacteria can cross contaminate each other. Moreover, cutting boards and butcher blocks contaminate various non-separated foods. Similarly, bacteria and microorganisms can contaminate and thrive on medical supplies and laboratory instruments. Blood, other body fluids, and growth media may mix and allow various microorganisms to cross contaminate each other. Various pathogenic bacteria such as *Escherichia coli* 0157: H7, *Listeria, Campylobacter, Salmonella, Shigella*, etc., can spread disease and cause sickness and even death. The present invention provides biocidal compositions useful to combat such pathogens.

The compositions of the present invention can saturate the surfaces of various articles, thus rendering the articles devoid of pathogenic organisms. In certain instances, the article is a medical surface, lab surface, or food contact surface or article. Various food contact surfaces and articles include, but are not limited to, an eating surface, a cutting board, a meat block, kitchenware and a floor.

VII. EXAMPLES

Example 1

This example illustrates the Antimicrobial Diffusion Test used to determine efficacy of a compound to inhibit microorganism growth.

FIGS. 1–5 depict a series of agar plates which demonstrate the effect of various compounds on a number of organisms. Assessment of the indicated compound is carried out according to the following protocol.

Figure 2:
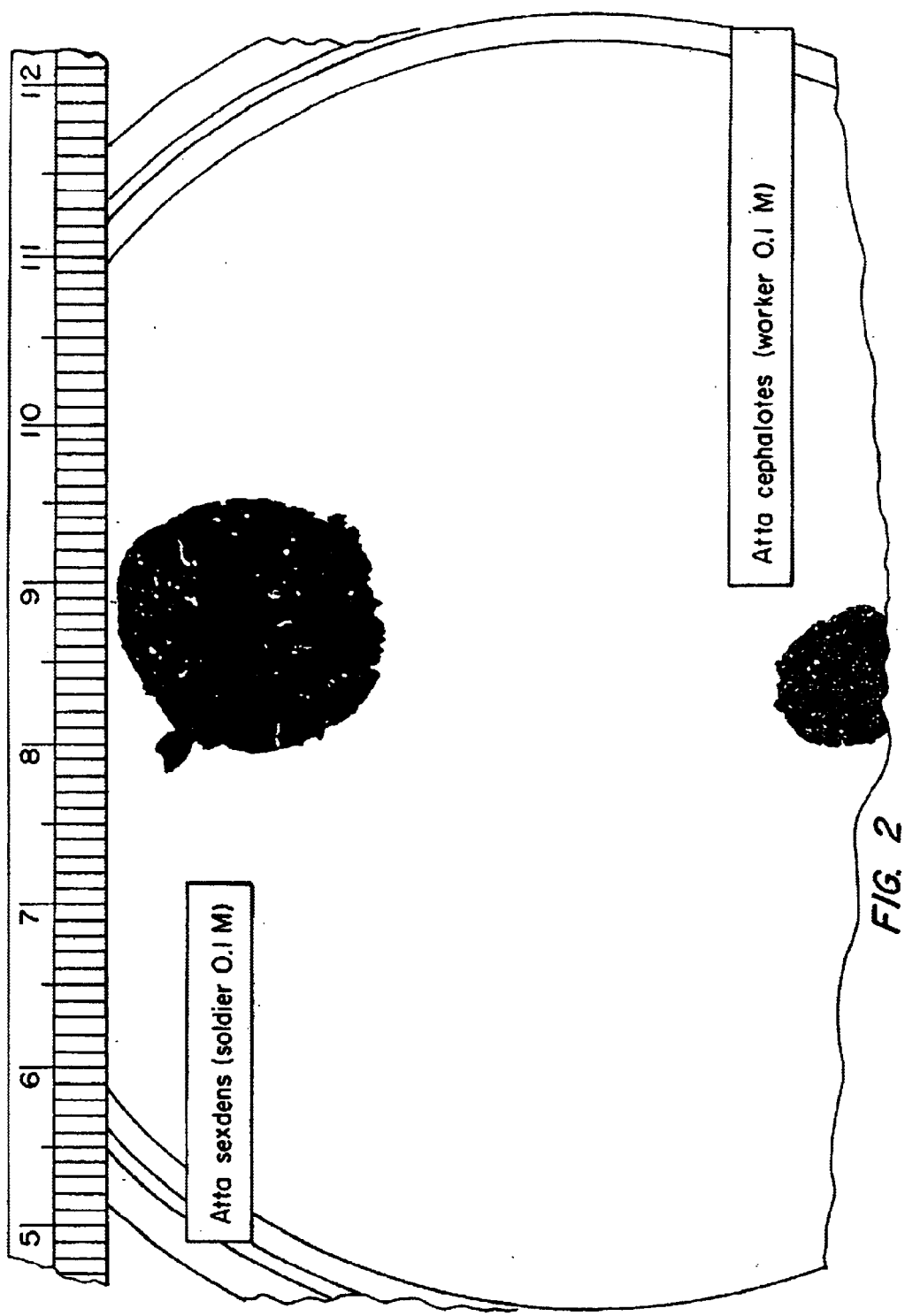
FIG. 2 illustrates the inhibitory effect of a composition of the present invention on *Candida albicans* growth.
Figure 3:
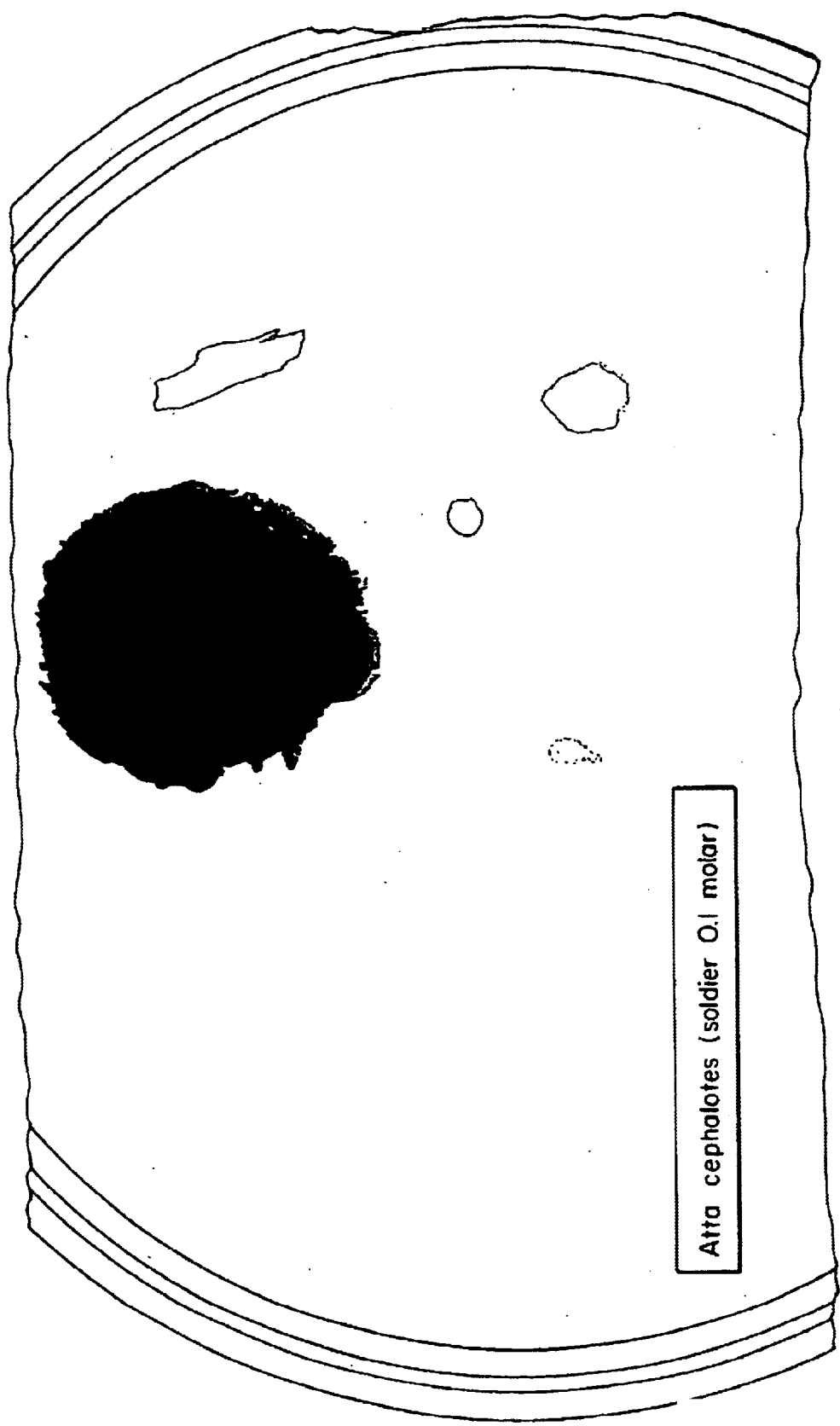
FIG. 3 illustrates the inhibitory effect of a composition of the present invention on *Beta Streptococcus* growth.
Figure 4:
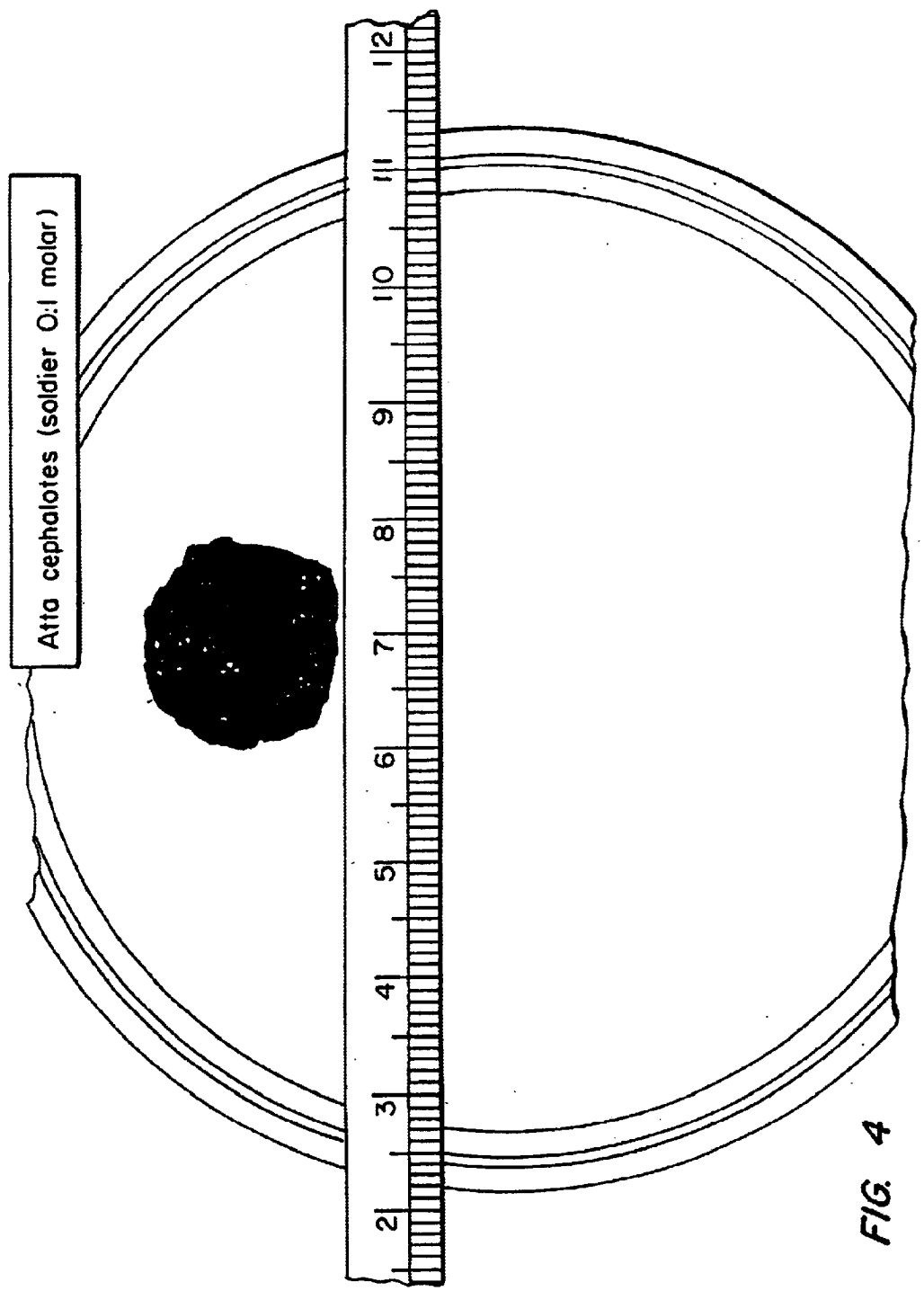
FIG. 4 illustrates the inhibitory effect of a composition of the present invention on *Escherichia coli* growth.
Figure 5:
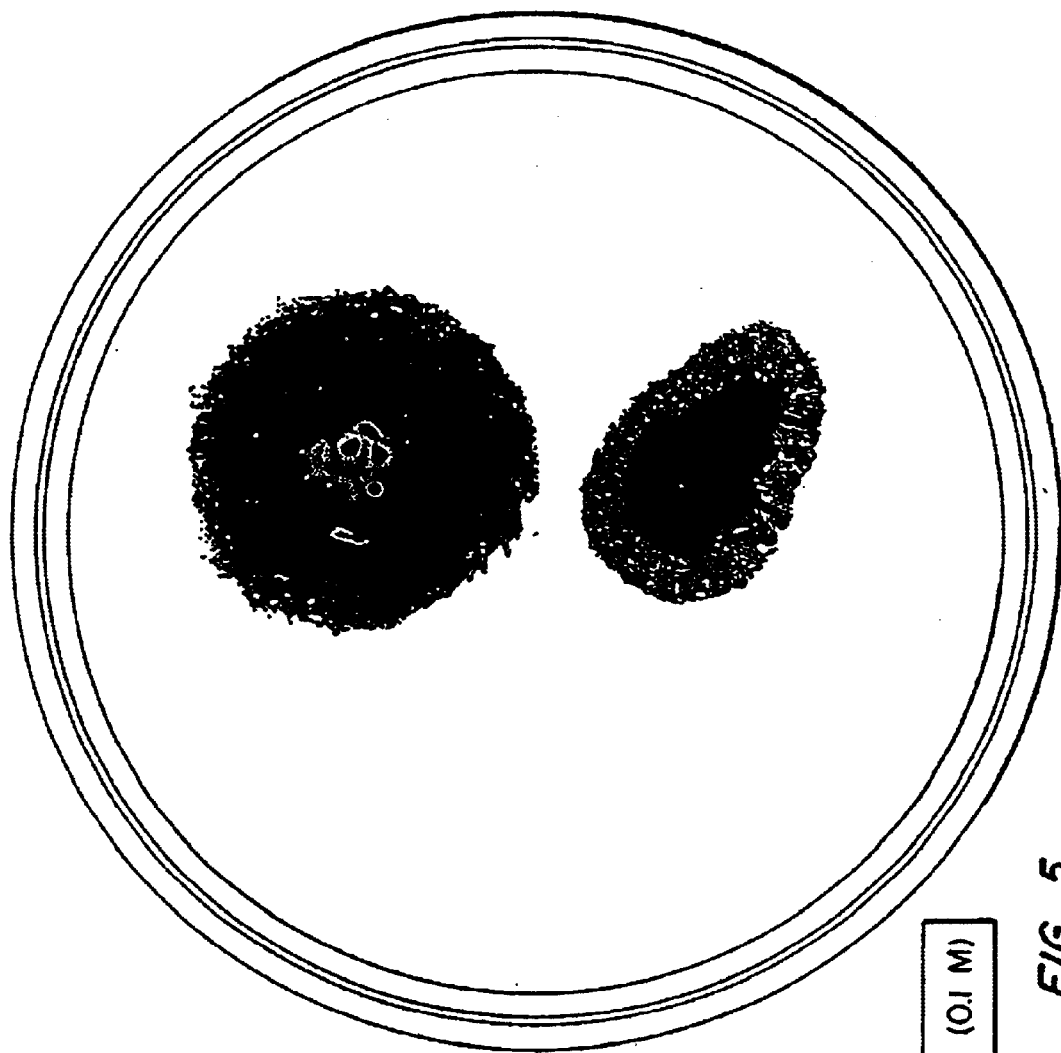
FIG. 5 illustrates the inhibitory effect of 3-pentylphenol on *Aspergillus fumigatus* growth.

FIG. 1 shows that a reconstituted metapleural gland extract from the ant *Atta sexdens* inhibits the growth of *Escherichia coli* in a significant area of agar plate. In the presence of a 0.1 M reconstituted *Atta sexdens* metapleural gland extract, growth of *Escherichia coli* was inhibited to a diameter of 1.4 cm of the applied extract, indicative of high sensitivity of the organism to this agent. FIG. 2 shows the inhibition of *Candida albicans* by a reconstituted 0.1 M *Atta cephalotes* metapleural gland extract. *Beta Streptococcus* growth is inhibited by a reconstituted 0.1 M metapleural gland extract from *Atta cephalotes*, as shown in FIG. 3. Similarly, a reconstituted 0.1 M *Atta cephalotes* metapleural gland extract inhibits growth of *Escherichia coli* (see, FIG. 4). 0.1 M 3-pentylphenol is effective at inhibiting *Aspergillus fumigatus* growth, as seen in FIG. 5.

The Antimicrobial Diffusion Test is used to determine the ability of a compound to inhibit growth of an organism. During the course of the test, each compound is treated as an unknown solution with an assigned number. After the data have been collected, the identity of the compound is assigned. In the test, a blood agar plate is inoculated with a known stock organism (fungus or bacteria). One drop of a numbered solution is applied to a freshly inoculated agar plate. A single numbered solution is applied per organism on a plate. The inoculated plate is examined on a daily basis for growth of the organism.

Areas of no microbial growth, or zones of inhibition are measured in millimeters and documented. If the plate is entirely covered with organism growth, there is no measurable zone of inhibition. After all zones of inhibition with the corresponding organisms and the solution number tested for sensitivity have been documented, each solution number is replaced by the correct solution name. The zones of inhibition are then used to establish relative in vitro resistance and sensitivity of the organism to the solution.

Example 2

This example illustrates the comparative effectiveness of various antimicrobial compounds.

Table 1 provides data comparing the efficacy of a number of different antimicrobial compounds of the present invention. Compounds were assayed at varying concentrations using the Antimicrobial Diffusion Test described above. Summary for data on the following compounds is listed: 3-n-propylphenol, 3-pentylphenol, 5-propylresorcinol, 4-hexylresorcinol, phenol, phenylacetic acid, 3-hydroxoctanoic acid, a reconstituted metapleural gland secretion from *Atta sexdens* worker ant, a reconstituted metapleural gland secretion from *Atta sexdens* soldier ant, a reconstituted metapleural gland secretion from *Atta cephalotes* worker ant, a reconstituted metapleural gland secretion from *Atta cephalotes* soldier ant, metapleural gland secretion from *C. deformis*, Mycocide, Tineacide, and Penlac. The compounds were tested for their ability to inhibit growth of the following organisms: *Candida alhicans, Staphylococcus aureus, Beta Streptococcus, Escherichia coli, Aspergillus fumigatus*, and *Trichophyton rubrum*. The numbers listed indicate relative potency of inhibition, with higher numbers representing greater ability to inhibit organism growth. Compounds such as 3-n-propylphenol and 3-pentylphenol have a broad specificity of inhibitory activities, and have the ability to inhibit growth of all organisms tested.

TABLE 1

INHIBITION DATA SUMMARY

| Compound (Concentration) | Candida Albicans | Staph aureus | Beta Strep | E. coli | Asp fumigatus | T rubium | pH |
|---|---|---|---|---|---|---|---|
| 1. 3-n-propylphenol (0.1 M) | 13 | 14 | 15 | 17 | 10 | 21, 14 | 6.5 |
| 2. 3-n-propylphenol (0.01 M) | 13 | | | | | 12 | 6.5 |
| 3. 3-pentylphenol (0.1 M) | 21 | 18 | 18 | 15 | 25 | 65, 45 | 6.5 |
| 4. 3-pentylphenol (0.01 M) | 15 | 14 | 15 | 16 | 9 | 16 | 6.5 |
| 5. 5-propylresorcinol (0.1 M) | 14 | | 14 | 15 | | 14 | 6.5 |
| 6. 5-pentylresorcinol (0.1 M) | 19 | 16 | 20 | 17 | 20 | 47 | 6.5 |
| 7. 4-hexylresorcinol (0.1 M) | 20 | 15 | 17 | 15 | 20 | 38 | 6.5 |
| 8. 4-hexylresorcinol (0.01 M) | 19 | 16 | 16 | 17 | 16 | 29 | 6.5 |
| 9. 3-hydroxoctanoic acid (0.1 M) | 12 | | 12 | 13 | | | 6 |
| 10. 3-hydroxydecanoic acid (0.1 M) | 15 | 12 | 11 | 13 | 13 | 12 | 6 |
| 11. indoleacetic acid (0.1 M) | | | 6 | | | | 6 |
| 12. 3-hydroxydecanoic acid (0.01 M) | | | 12 | | | | 6.5 |
| 13. 3-hydroxydodecanoic acid (0.01 M) | | | | | | 10 | 6.5 |
| 14. 3-hydroxydodecanoic acid (0.1 M) | 8 | 9 | 10 | 10 | 7 | 14 | 6 |
| 15. Atta sexdens (worker 0.1 M total components) | 13 | 14 | 15 | 15 | 14 | 13 | 6 |
| 16. Atta sexdens (soldier 0.1 M total components) | 16 | | 12 | 15 | | 15 | 6 |
| 17. Atta cephalotes (worker 0.1 M total comp.) | | | 9 | | | | 6 |
| 18. Atta cephalotes (soldier: 0.1 M total comp.) | 17 | 15 | 16 | 18 | | 16 | 6 |
| 19. C. deformis (0.1 M total components) | 15 | 12 | 14 | 13 | 13 | 20 | 6.5 |
| 20. C deformis (0.01 M total components) | 12 | | 9 | | | 12 | 6.5 |
| 21. Mycoside | 20 | | | | 21 | 24 | |
| 22. Tineacide | 24 | | | | 25 | 58 | |
| 23. Penlac, undiluted | 32 | | | | 37 | 48 | |
| 24. Penlac, 0.1 M | 33 | | | | 35 | 46 | |
| 25. Penlac, 0.01 M | 18 | | | | 19 | 22 | |

Example 3
Treatment of Onychomycosis by Topical Administration of 3-Pentylphenol—A Clinical Trial This example illustrates the treatment of patients with onychomycosis with 3-pentylphenol.

Patients may have a combination of the following subtypes of onychomycosis: distal lateral subungual onychomycosis (DLSO), white superficial onychomycosis (WSO), proximal subungual onychomycosis (PSO), endonyx onychomycosis (EO) and Candida onychomycosis. The patient presents acutely with physical characteristics such as discoloration of the nail plate, roughened nail surface, bulbous digits, etc. Diagnosis is confirmed by clinical laboratory and pathological diagnostic tests, including direct microscopy, culture, immunohistochemistry and dual flow cytometry.

For treatment of onychomycosis, a composition comprising 3-pentylphenol is applied to the affected toenails at a dosage of 250 mg twice a day for 12 weeks. The composition is applied evenly over entire nail plate and 5 mm of surrounding skin 8 h before washing. The composition is applied to the nail bed, hyponychium, and under surface of nail plate when free of nail bed. The composition is not removed on a daily basis, and daily applications are made over the previous coat and removed with alcohol once a week. This regimen is repeated throughout the duration of therapy. Regression of the disease or improvement in clinical status is evaluated by monitoring improvement in nail-plate appearance. Reduction in microorganism growth is assessed by direct microscopy, culture, immunohistochemistry and/or dual flow cytometry.

Example 4
Combination Treatment of Onychomycosis by Topical Administration of An Antimicrobial Compound and Itraconazole—A Clinical Trial This example illustrates the treatment of individuals with onychomycosis with an antimicrobial compositions in combination with oral therapy.

The disease is selected from one of the following: DLSO, WSO, PSO, EO and Candida onychomycosis. The antimicrobial composition comprises a compound selected from: 3-n-propylphenol (250 mg twice daily topical dose), 3-pentylphenol (250 mg twice daily topical dose) and 3-hydroxydecanoic acid (250 mg twice daily topical dose). These pharmacological compositions may be used to treat acute or chronic disease or may be used prophylactically to prevent the onset of the disease.

The patient presents acutely with physical characteristics of onychomycosis such as discoloration of the nail plate, roughened nail surface, bulbous digits, etc. Diagnosis is confirmed by clinical laboratory and pathological diagnostic tests, including direct microscopy, culture, immunohistochemistry and dual flow cytometry. Provided that the patient is not pregnant and does not plan to become pregnant during treatment, a compound known to inhibit microorganism growth, namely itraconazole is administered orally in a dosage of 200 mg once daily for 12 consecutive weeks in combination with topical treatment described above. Regression of the disease or improvement in clinical status is evaluated by monitoring standard clinical indicators.

The patien's response to therapy is monitored by direct microscopy analysis and culture analysis to monitor amelioration of the microorganism infection to assess clinical improvement.

Example 5
Comparative Example. The Compositions of the Present Invention are more Efficacious Compared to Known Treatment for Onychomycosis.

The present standard of care for treatment of onychomycosis is Penlac.

Table 1 in Example 2 provides data comparing the efficacy of a number of different antimicrobial compounds of the present invention. As shown, 3-pentylphenol at a concentration of 0.1M (row 3) has exceptional broad spectrum effectiveness on the microorganisms tested. Side-by-side comparative results against Penlac at a concentration of 0.1M (row 27) shows that the composition of the present invention is unexpectedly superior against *Trichophyton rubrum*, one of the most common causes of onychomycosis.

Example 6

The Compositions of the Present Invention Include Ant Metapleural Gland Secretions.

The ant metapleural gland secretions from 1000 ants of each of the following species are collected in fine glass capillaries: *Atta cephalotes, Acromyrmex octospinosus*, and *Crematogaster deformis*.

The larger end of the capillary is attached to a 10 µl syringe needle with a silicone tubing connection. The wall of the bulla of the metapleural gland is pierced with a fine insect-mounting pin, and the ant is then held so the fine tip of the capillary is inserted into the hole in the bulla, and the secretion is withdrawn into the capillary by gently raising the plunger of the syringe. The secretions are collected and pooled.

The secretion of each ant species is analyzed by GCMS. Table 2 sets forth the 3 major components of each of the species.

TABLE 2

| ANT | MAJOR COMPONENTS | | |
|---|---|---|---|
| *Atta cephalotes* | phenylacetic acid | indoleacetic acid | Skatole |
| *Acromyrmex octospinosus* | 3-hydroxydecanoic acid | indoleacetic acid | |
| *Atta sexdens rubropilosa* | phenylacetic acid | 3-indoleacetic acid | 3-hydroxy-decanoic acid |
| *Crematogaster deformis* | 3-propylphenol | 3-pentylphenol | Mellein |

The collected secretion is used directly.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating onychomycosis in a mammal, said method comprising:

contacting said mammal with a biocidally effective amount of a composition comprising: a combination of at least one compound of Formula Ia and at least one compound of Formula II, wherein Formulae Ia and II have the Formulae:

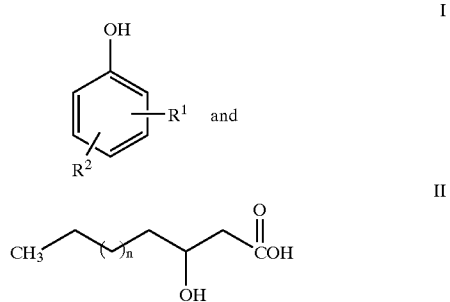

wherein:
$R^1$ is an optionally substituted alkyl;
$R^2$ is hydrogen; and,
n is about 0–6, or a salt or ester thereof of Formula II; and an excipient therefor, to treat onychomycosis.

2. The method of claim 1, wherein the composition comprises 3-propylphenol, 3-pentylphenol and 3-hydroxydecanoic acid.

3. The method of claim 1, wherein said composition inhibits the growth of a member selected from the group consisting of *Trichophyton rubrum, Candida albicans, Aspergillus fumitgatus, Staphylococcus aureus, Beta Streptococcus*, and *Escherichia coli*.

4. The method of claim 1, wherein said method further comprises the treatment of a member selected from the group consisting of *Tinea pedis, Tinea unguium, Tinea cruris*, and *Tinea capitis*.

5. The method of claim 1, wherein $R^1$ is $C_1$–$C_8$ alkyl.

6. The method of claim 5, wherein $R^1$ is $C_3$–$C_7$ alkyl.

7. The method of claim 5, wherein $R^1$ is propyl.

8. The method of claim 5, wherein $R^1$ is butyl.

9. The method of claim 5, wherein $R^1$ is pentyl.

10. The method of claim 5, wherein $R^1$ is iso-butyl.

11. The method of claim 1, wherein said compound of Formula II is 3-hydroxydecanoic acid.

* * * * *